United States Patent [19]
Pero

[11] Patent Number: 5,561,129
[45] Date of Patent: Oct. 1, 1996

[54] METHODS OF ADMINISTERING PHENOTHIAZINES AND/OR ACID ADDITION SALTS THEREOF

[75] Inventor: Ronald W. Pero, Lund, Sweden

[73] Assignee: OXiGENE, Inc., New York, N.Y.

[21] Appl. No.: 479,113

[22] Filed: Jun. 7, 1995

Related U.S. Application Data

[62] Division of Ser. No. 218,072, Mar. 25, 1994.

[51] Int. Cl.$^6$ ..................................................... A61K 31/54
[52] U.S. Cl. ............................................................ 514/224.8
[58] Field of Search ............................................. 514/224.8

[56] References Cited

PUBLICATIONS

Hancoq, M., et al. "Determination des Constantes d'acidite ...," *J. Pharm. Belg.* vol. 28, pp. 649–662 (1973).
Pero et al., "Progress in identifying clinical relevance ..." Biochimie, 77, pp. 385–393 (1995).
King, F. D., et al. "SHT, Receptor Antagonists, *Drugs of the Future*", vol. 14, pp. 875–889 (1989).
Van deWaterbeemd, H., et al. "Similarities of pharmacophoric pattern . . . ," J. Molec. Graphics, vol. 4, pp. 51–55 (1986).
Ammar et al., Pharmazie 30(6) pp. 368–369 (1975).

*Primary Examiner*—Phyllis G. Spivack
*Attorney, Agent, or Firm*—Cooper & Dunham LLP

[57] ABSTRACT

A method of administering phenothiazines and their acid addition salts. The phenothiazine or acid addition salt is injected intramuscularly in a formulation with a pH of about 5.5 to about 7.0 and at a concentration of at least about 50 mg/ml, to deliver a dose of one to 5 mg/kg. The drug is administered either in a formulation containing $Na^+$ ions and at a pH adjusted to reduce extrapyramidal side effects or in a formulation essentially free of $Na^+$ ions.

8 Claims, 2 Drawing Sheets

• log i.m.  y = 0.24295 − 2.4105e−3x   R^2 = 0.834 · T1/2 = 125 min
○ log i.v.  y = 0.27362 − 2.7163e−3x   R^2 = 0.999 · T1/2 = 110 min

METHODS OF ADMINISTERING PHENOTHIAZINES AND/OR ACID ADDITION SALTS THEREOF

This is a division of application Ser. No. 218,072, filed Mar. 25, 1994 allowed.

BACKGROUND OF THE INVENTION

This invention relates to methods of administering pharmaceutical materials, in particular N-substituted benzamides, phenothiazines, and acid addition salts thereof, to human patients, as well as to formulations containing such materials. In an important specific sense, to which detailed reference will be made herein for purposes of illustration, the invention is directed to methods and formulations for administering acid addition salts of metoclopramide to human patients.

Metoclopramide is currently available in acid addition salt form, as metoclopramide hydrochloride, for administration to human patients as an antiemetic (e.g., in conjunction with chemotherapy) and for other purposes. It has also been discovered that metoclopramide and other N-substituted benzamides and their acid addition salts can enhance the cytotoxicity of chemotherapeutic agents and radiation. Commercially available formulations of metoclopramide hydrochloride are in physiologic saline solution, to which sodium metabisulfite has sometimes been added as a preservative. Typically or conventionally, these formulations are prepared for intravenous (i.v.) injection or oral administration.

The commercial formulations of metoclopramide hydrochloride have pH ranges within outer limits of about 2 to 6.5, depending inter alia on concentration. At least within these limits, it has been considered that the pH of the formulation does not affect the biological activity of the drug. A reason for the acidity of the formulations is that the acid addition salts of metoclopramide are freely soluble in aqueous vehicles whereas the free-base form is quite insoluble in water.

Although some commercial metoclopramide formulations are sold with an indicated pH range extending up to 6.5, in fact the pH of such formulations tends to be variable and/or unstable within that range and is commonly substantially below 6.5 at least by the time the formulation is administered to a patient, owing, for instance, to autooxidation effects. Moreover, the formulations with a nominal pH ranging up to 6.5 are highly dilute, e.g. having a metoclopramide hydrochloride concentration of 5 mg/ml. Present-day commercial formulations with significantly higher concentrations, exemplified by 100 mg/ml, have pH values of 4.5 or less.

Heretofore it has been found that metoclopramide acid addition salts in known formulations can have extrapyramidal side effects when administered to humans. These effects are undesirable and, in some instances, may restrict or prevent use of the drug.

In specific aspects, the present invention relates to the bioavailability of intramuscular (i.m.) injections of metoclopramide and its acid addition salt forms. More particularly, this invention relates pH adjustment of acid addition salt solutions of N-substituted benzamides and phenothiazines such as metoclopramide to altered biological responses important to the development of undesirable side effects of these types of drug for clinical use to prevent emesis or to enhance radio- and chemotherapies such as the local tissue toxicity at the site of i.m. injection or reduction in the extra-pyramidal side effect of sedation.

Metoclopramide and other pharmacologically active N-substituted benzamides and phenothiazines are offered in commercial form as acid addition salts (1993 Physician's Desk Reference), presumably because this form is freely soluble in aqueous solution whereas the free base form is quite water insoluble. Hence, the acid addition salts of metoclopramide and other N-substituted drugs are pharmaceutically superior forms for bioavailability via a variety of routes of administration.

U.S. Pat. No. 4,888,354 teaches that "By employing a free base-acid addition salt mixture of active ingredients, it has been found that penetration enhancement of the active ingredient is greatly improved as compared to use of either the free base or acid addition salt alone at the same concentration levels. In most cases, the rate of penetration is greater than the sum of the base and acid addition salt when applied separately." The endpoint used was skin penetration of metoclopramide. This prior art is clearly distinguished from the present invention in that it pertains only to penetration of drug through skin membranes and not to any biological response modification associated to either the base or acid addition salt forms of metoclopramide or any combinations thereof.

U.S. Pat. No. 4,536,386 discloses that "High doses of metoclopramide or a pharmaceutical salt thereof is administered intravenously to human cancer patients undergoing cisplatin chemotherapy to prevent emesis." This patent teaches that either metoclopramide (by implication the base) or an acid addition salt can inhibit the biological response of emesis, but it does not teach that any combination of these two forms would either enhance or inhibit emesis. Furthermore, it was emphasized that the commercial metoclopramide acid addition salt formulation containing physiologic saline (Reglan, a product of Robbins) was the preferred form of the drug for intravenous injection. There was no recognition of the concept that the sodium chloride present in the formulation of metoclopramide might influence the antiemetic effects compared to either the pure acid addition salt or free base forms, or that pH adjustment of acid addition salt formulations of metoclopramide might produce superior antiemetic effects or mediate reduced extrapyramidal side effects.

European patent application No. 88201795.7 and several other recent scientific reports (Kjelle'n et al., Br. J. Cancer 59: 247–250, 1989; Lybak et al., Int. J. Rad. Oncol. Biol. Phys. 19: 1419–1424, 1990; Lybak et al., Anti-Cancer Drugs 2: 375–382, 1991; Lybak et al., Acta Oncologica 31: 469–474, 1992; Salford et al., Anti-Cancer Drugs 3: 267–272, 1992) have also revealed that a commercial preparation of a metoclopramide acid addition salt (Lundbeck AB, Copenhagen) can enhance the cytotoxic action of radiation and several chemotherapy drugs. However, again these reports did not disclose whether the base or acid addition salt forms of metoclopramide or the presence of other formulation ingredients such as sodium chloride or sodium metabisulfite could modify in any way the biological response of radio- or chemotherapeutic sensitization or influence the extrapyramidal side effects of the drug.

SUMMARY OF THE INVENTION

The present invention, in a first aspect, contemplates the provision of a method of administering to a human patient material selected from the group consisting of N-substituted benzamides, their acid addition salts, phenothiazines, their acid addition salts, and mixtures thereof, comprising the steps of providing a sterile injectable formulation comprising a liquid vehicle containing the material in solution and injecting the formulation intramuscularly into the patient in an amount for delivering to the patient a dose of about one to about 5 mg/kg of the material. In important embodiments of this method, the material to be administered is metoclopramide (which is an N-substituted benzamide), conveniently or preferably in the acid addition salt form, e.g. as metoclopramide hydrochloride.

Intramuscular injection affords various advantages (such as ease of injection as compared with i.v. injection, especially for repeated doses) over other modes of administration in particular situations. Offsetting these advantages is the expected difference in rate of availability within the patient's system between i.v. and intramuscular injections. Because a dose administered by intramuscular injection is not introduced directly to the bloodstream, it would be expected to be distributed and delivered to tissues under treatment more slowly than the same dose administered by i.v. injection. Surprisingly, however, it has now been found that the rate of availability of a given dose of metoclopramide (e.g. as the acid addition salt) administered by intramuscular injection is comparable to that of the same dose administered by i.v. injection, for a useful range of doses, viz. about one to about 5 mg of metoclopramide per kg of patient body weight ("mg/kg"). Thus, intramuscular injection of metoclopramide, with its attendant advantages, is fully equivalent in treatment efficacy to i.v. injection.

Intramuscular injection, to achieve a dose of 1–5 mg/kg, requires a much more concentrated formulation than i.v. injection of a like dose, owing to the limited tolerance of muscle tissue for injected fluid. Whereas a solution at a 5 mg/ml concentration of metoclopramide hydrochloride is suitable for i.v. injection of a dose of 5 mg/kg, a concentration of at least about 50 mg/ml or even more (preferably, in many cases, as much as 100 mg/ml) is needed to administer a like dose by intramuscular injection. At these high concentrations, present-day commercial metoclopramide formulations tend to produce local tissue toxic reactions at the injection site.

Further in accordance with the invention, a concentrated metoclopramide (e.g. metoclopramide hydrochloride) formulation is advantageously provided at a pH of about 5.5 to 7.0, for intramuscular injection. At pH values within this range (which is substantially higher, i.e. less acidic, than the pH of currently available formulations of equivalent concentration), local tissue toxic reactions are satisfactorily minimized or avoided, yet without adversely affecting the solubility of the metoclopramide or its therapeutic activity. A pH above 7.0 would derogate from solubility, while values below about 5.5 are insufficient to achieve the desired reduction in local tissue side effects.

In a second aspect, the invention contemplates the provision of a sterile injectable metoclopramide formulation for intramuscular administration to a human patient, comprising a material selected from the group consisting of metoclopramide, acid addition salts of metoclopramide, and mixtures thereof; a liquid vehicle in which the material is in solution; the material being present in the formulation in a concentration of at least about 50 mg/ml; and the formulation being at a pH within a range of about 5.5 to 7.0. In these formulations, the solution pH, once established, may be stabilized to a less variable range (e.g. <0.5 pH unit) by the inclusion of a phosphate or other buffer, or alternatively, by the inclusion of a preservative such as sodium metabisulfite to prevent auto-oxidation.

Also surprisingly, it has been found that the administration of metoclopramide hydrochloride in otherwise-conventional formulations (which contain $Na^+$ ions, present in the saline solution and/or introduced as sodium metabisulfite) but at a pH of about 5.5 to 7.0 substantially prevents the extrapyramidal side effects of known metoclopramide treatments. In a third aspect, which is not limited to intramuscular injection, the invention contemplates the provision of a method of administering to a human patient material selected from the group consisting of N-substituted benzamides, their acid addition salts, phenothiazines, their acid addition salts, and mixtures thereof, comprising the steps of providing a formulation, comprising a liquid vehicle containing the material in solution and also containing $Na^+$ ions, adjusting the pH of the formulation for reducing the development of undesirable side effects of the material, and administering the formulation having the adjusted pH to the patient. A preferred or effective range of formulation pH for reduction or avoidance of antipyramidal side effects is between about 5.5 and about 7.0.

It has additionally now been found that the occurrence of extra-pyramidal side effects in metoclopramide treatment is associated with the presence of $Na^+$ ions in a substantially acidic (pH below about 5.5) solution. As an alternative to the pH adjustment just described, the invention in yet another aspect contemplates the provision of a method of administering to a human patient material selected from the group consisting of N-substituted benzamides, their acid addition salts, phenothiazines, their acid addition salts, and mixtures thereof, comprising the steps of providing a formulation comprising a liquid vehicle containing the material in solution and essentially free of $Na^+$ ions, and administering the formulation, essentially free of $Na^+$ ions, to the patient. The vehicle may conveniently be water. The term "essentially free of $Na^+$ ions" means free of any deliberately introduced source of $Na^+$ ions, e.g. physiologic saline or sodium metabisulfite, and excludes the presence of any content of $Na^+$ ions sufficient to produce undesired extrapyramidal side effects when the formulation is administered at a pH of about 4.2.

Further features and advantages of the invention will be apparent from the detailed description hereinbelow set forth, together with the accompanying drawings.

DETAILED DESCRIPTION

Figure 1A:
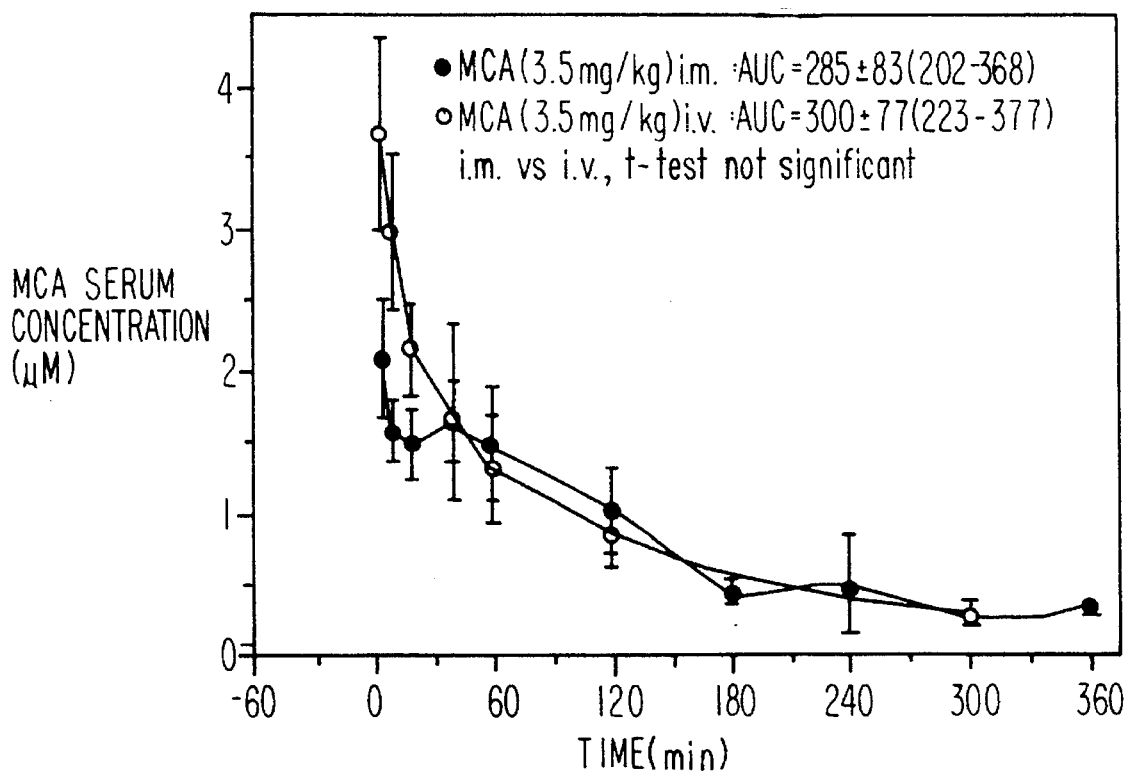
FIG. 1A is a graph on which serum concentration of metoclopramide ("MCA") is plotted against time after injection, for intramuscular ("i.m.") and i.v. injection of 3.5 mg/kg doses of metoclopramide.

As hereinafter described in detail, the invention embraces embodiments involving the use of i.m. injection as a dose equivalent alternative to i.v. injection to deliver 1–5 mg/kg doses of metoclopramide or an appropriate acid addition salt or combinations thereof to individuals being treated for emesis or to enhance radio- and chemotherapy of cancer.

The invention also is embodied in methods involving the use of pH adjustment of N-substituted benzamide and phenothiazine acid addition salt solutions, such as sterile injectable formulations of metoclopramide containing biologically compatible inorganic salts such as sodium chloride or sodium metabisulfite, to reduce the development of undesirable side effects of the drug without affecting the pharmacological properties of emesis or the enhancement of radio- and chemotherapies of cancer.

In addition, the invention is embodied in methods involving the use of preparing aqueous sterile injectable formulations of N-substituted benzamide and phenothiazine acid addition salts free from inorganic salts such as sodium chloride and sodium metabisulfite, and with or without pH adjustment, in order to avoid undesirable side effects of the drug without affecting the pharmacological properties of emesis or enhancement of radio- and chemotherapies of cancer.

The bioavailability and pharmacokinetics of a drug are extremely important biochemical measures of how effectively a drug is absorbed, distributed and eliminated from the body (Pharmacokineric principles in the use drugs, in Medical Pharmacology, A. Goth ed., C.V. Mosby Company, tenth edition, St. Louis, Mo., pages 15–30, 1981). The level of a drug in serum in reference to the time of administration has been shown to be a reliable indicator of how the drug is metabolized and in relation to any toxicological or pharmacological properties. The basic pharmacological principles are further complicated by having various possible routes of administration. For example, some common routes of drug administration used in clinical medicine are intravenous (i.v.), intramuscular (i.m.) and subcutaneous (s.c.) injection or by oral consumption. The concept of bioavailability is therefore needed to define any differences in the absorption of a drug when it must first be absorbed by different tissues before it can be measured in serum; e.g. the digestive tract for oral administration and muscle tissue for i.m. administration. Of course, this is not true for i.v. administration of a drug, where 100% of the administered dose is immediately available for tissue absorption and distribution. Hence prior art based on the pharmacological principle of bioavailability defines that a drug administered by oral, i.m. or s.c. routes would have different pharmacokinetic parameters (e.g. longer elimination time) than when the same drug was administered i.v. As a consequence, any altered pharmacokinetic parameters due to route of administration would, in turn, be expected by one skilled in the art to alter the clinical effectiveness of the pharmacological properties of the drug.

The present invention embraces the discovery that metoclopramide, a drug used to treat emesis and to enhance conventional radio- and chemotherapies of cancer, has such a rapid and efficient absorption from muscle tissue into blood, that there are no significant differences in metoclopramide serum levels between administering the same dose of metoclopramide either by i.v. or i.m. injection. To our knowledge, there are no published reports of metoclopramide or of any other drugs demonstrating i.m. and i.v. dose equivalency. The knowledge that there is near dose equivalency between the i.v. and i.m. routes of administration of metoclopramide is useful information because it teaches that even though only the i.v. route has been used previously to administer high dose metoclopramide (i.e 1–2 mg/kg) as an antiemetic, the i.m. route would be equally effective without major changes in dose scheduling events.

In another aspect, the practice of this invention involves consideration of the pH of metoclopramide solutions. The 1993 Physicians' Desk Reference lists only the metoclopramide hydrochloride salt form as available for clinical use. Metoclopramide hydrochloride salts are freely soluble in water, but these solutions are quite acidic ranging in pH from 2 to 6.5 depending on the initial drug concentration and formulation ingredients (American Society of Hospital Pharmacists, 1993; Sveriges Läkersmedels Information AB, FASS 1993). Metoclopramide hydrochloride is commercially available worldwide in injectable form as a 5 mg/ml injectable solution (e.g. from Robbins, DuPont, Goldline, Schein, Smith and Nephew Solopak, Adria), and as a 100 mg/ml injectable concentrate in Scandinavia (Lundbeck AB) for dilution with sterile physiologic saline and subsequent i.v. infusion at final doses up to 5 mg/kg for the treatment of emesis. In order to deliver doses of 1–5 mg/kg by i.m. injection to patients, the injectable formulations would require initial metoclopramide hydrochloride concentrations of around 100 mg/ml, which is a drug concentration having a pH range of 2 to 4.5 depending on its formulation (American Society of Hospital Pharmacists, 1993; FASB, 1993). Because commercial preparations of metoclopramide hydrochloride solutions drastically vary in pH, and because they can be pH adjusted from 2 to 6.5 without regulatory restrictions, the prior art teaches that there is no difference in biological activity associated with changes in pH between 2 and 6.5. However, this invention teaches that when acidic formulations of metoclopramide hydrochloride solutions within a pH range of 2 to 3.7 are compared to a neutralized formulation at pH 7.0, the local tissue toxic reaction at the site of i.m. injection and the extra-pyramidal side effect of sedation, are substantially reduced when the neutralized formulation is administered. Hence, this invention demonstrates that high concentrations of metoclopramide hydrochloride (e.g.100 mg/ml), which would be required for i.m. administration of metoclopramide as an antiemetic or radiosensitizer at 1–2 mg/kg, have fewer toxic side effects in the near neutral pH range than in the acidic form, which is currently the only clinically available form of the drug.

The scientific explanation behind these pH dependent biological effects of metoclopramide hydrochloride solutions is not at present known. However, the data presented in support of this invention have established that sterilized solutions of metoclopramide, which contained sodium ions in the form of sodium chloride or sodium metabisulfite in the injectable formulations, caused amplification of both local and systemic drug side effects when the pH of the formulations was 2 to 4.5 compared to when it was adjusted to 5.5 to 7.0. These results implicate a chemical interaction between sodium ions and metoclopramide under acidic conditions (i.e. below pH 4.5), but not at more neutralized conditions (i.e. pH 5.5–7.0), which in turn modulates in a corresponding manner at least some of the extra-pyramidal and local side effects caused by the drug.

Metoclopramide is known to bind to both the dopamine$_2$ (D$_2$) receptor as well as the 5-hydroxytryptamine$_3$ (5-HT$_3$) receptor (Harrington et al., Drugs 25: 451–494, 1983; Blower, Eur. J. Cancer 26 (Suppl.1): S8–S11, 1990). The extra-pyramidal side effects of metoclopramide are believed to be derived from the D$_2$ receptor whereas the anti-emetic effects are generated from binding to the 5-HT$_3$ receptor (King and Sanger, Drugs of the Future 14(9): 875–889, 1989). Moreover, the binding of metoclopramide to the $D_2$ receptor has been shown to be sodium ion dependent (Theodorou et al., J. Pharm. Pharmacol. Commun. 32: 441–444, 1980). These data from the scientific literature support and are consistent with the altered systemic biological effects of metoclopramide observed in the presentation of this invention. However, it would have been an unexpected observation for one skilled in the art to have been able to predict that metoclopramide in combination with sodium ions under defined acidic conditions could form a chemical interaction stable enough to be transported from the site of intramuscular injection to the D2 receptors in the brain in order to mediate an enhanced sedative side effect.

Dose equivalency of i.v. and i.m. routes of administration of metoclopramide were determined by using a commercial preparation of metoclopramide hydrochloride appropriately diluted with sterile physiologic saline (100 mg/ml sterile infusion concentrate at pH 2 to 3.5, Lundbeck AB, Copenhagen; see ingredients of commercial product below). Final doses of metoclopramide of 3.5 mg/kg were delivered into Wistar/Furth rats (200–400g m) (i) by i.m. injection in the hind leg in volumes of 100 μl and, (ii) by i.v. infusion via the caudal vein in volumes of 250 μl over a 5–7 min period. About 0.5 ml of blood was removed by intraocular puncture at 5, 10, 20, 30, 40, 60, 120, 180, 240, 300 and 360 min. Serum samples were collected from the blood samples by centrifugation, and then they were prepared and analyzed for the presence of metoclopramide according to the procedure of Meyer et al. (Ann. Int. Med. 100: 393–395, 1984). Serum metoclopramide levels were quantified against an internal standard of haloperidol.

Acidic and neutral forms of metoclopramide hydrochloride solutions reported on in Examples 1–6 below were prepared from a commercial preparation (100 mg metoclopramide hydrochloride, 2 mg sodium metabisulfite, 1 ml distilled water, and prepared as a sterile infusion concentrate, Lundbeck AB, Copenhagen). The hundbeck AB preparation of 100 mg/ml, which was diluted with physiologic saline when necessary, had pH values between 2 and 3.5, and it served as the acidic form. The neutralized form was created by adjusting the pH of the Luridbeck formulation with i M NaOH to 7.0 after dilution with physiologic saline to 10–30 mg/ml before pH adjustment. The metoclopramide solutions reported on in Example 7 were prepared as indicated in Table 4 (Example 7) from analytical grade metoclopramide hydrochloride (Sigma), sodium metabisulfite (Sigma), and sodium chloride solution (9 mg/ml, Kabi Pharmacia). The pH adjustment of laboratory solutions of metoclopramide was with 1M HCl or 1M NaOH.

Differential biological responses estimated by the local tissue reaction in Fisher 344 rats following i.m. administration of acidic and neutral forms of metoclopramide hydrochloride solutions were determined by injecting 50–100 μl of saline into the right thigh and 50–100 μl of drug into the left one. The injections were repeatedly administered every other day except weekends (i.e. 3 times/week) within a previously identified 1 cm diameter area of the leg. After 10 injections or to the development of acute symptoms, the animals were sacrificed, muscle specimens were dissected from the injection area, formalin fixed and sectioned for histopathological examination.

Symptoms of local tissue reaction to high dose i.m. injection of acidic and neutral forms of metoclopramide hydrochloride solutions were evaluated as: ++++=all animals have >1 cm discoloration and stiffness in the injection area, pain to touch; +++=all animals have 0.5–1 cm discoloration and stiffness in the injection area, pain to touch; ++=<0.5 cm discoloration, stiffness and pain detectable in all animals; +=some animals have slight discoloration but no stiffness or pain in the injection area; 0=no observed symptoms. Acute histopathology of the local tissue reaction to high dose i.m. injection of acidic and neutral forms of metoclopramide hydrochloride solutions were evaluated as: Edema, acute inflammation, bleeding and necrosis where a 3 to 0 score was given with 3 being the strongest pathological reaction. The data are presented as the average for the total number of treated rats (n) calculated as the total score for each criterium divided by n. The pathologist scoring the acute histopathologywas blinded to the treatment protocol.

Chronic histopathology of the local tissue reaction to high dose i.m. injection of acidic and neutral forms of metoclopramide hydrochloride solutions were evaluated as: Chronic inflammation and muscle degeneration that occurred as a consequence of repeated i.m. injections in the same area of the thigh of the rat. Each criterium was given a 3 to 0 score where 3 was the strongest pathological reaction. The data are presented as the average for the total number of treated rats (n) calculated as the total score for each criterium divided by n. The pathologist scoring the chronic histopathology was blinded to the treatment protocol.

Lack of any measurable difference in the radiosensitizing properties of the acidic and neutral forms of metoclopramide hydrochloride solutions was evaluated in immune deficient Scid mice xenografted with a human lung adenocarcinoma (H-2981). Tumor tissue suspensions were prepared and inoculated subcutaneously into the midback region of 3–5 week old Scid mice so that 10 mm×10 mm tumors were grown in about 25 days. When the tumors were palpable usually 10–13 days after inoculation, the animals received 2 mg/kg of either acidic or neutral metoclopramide hydrochloride solutions by i.m. injection in a final volume of 100 μl (Lundbeck's 100 mg/ml infusion concentrate appropriately diluted with physiologic saline) at −1 hour or −2 hours to the ± irradiation treatment of 1 Gy. The tumor volumes were measured and recorded every 2–3 days and analyzed by a t-test at day 17 after inoculation.

The sedative effects induced systemically after i.m. injection of metoclopramide were evaluated in Fischer rats at a dose of 14 mg/kg 15 minutes post administration of the drug. The rats were placed at the entrance of a 8×10×45 cm tunnel located on top of a lab bench which was situated in an artificially lighted room free from external stimuli such as in view Of windows or other animals. only the top of the tunnel was transparent for observation purposes, and the end of the tunnel was left open as an escape stimulus. Immediately after each rat was released at the tunnel entrance, the time to negotiate the tunnel was recorded in seconds. Rats taking more than 60 seconds were no longer timed and these times were recorded as >60 seconds. The rats used in these experiments were not previously trained to negotiate the tunnel.

The following examples are given for the purpose of illustrating the present invention.

EXAMPLE 1

Figure 1B:
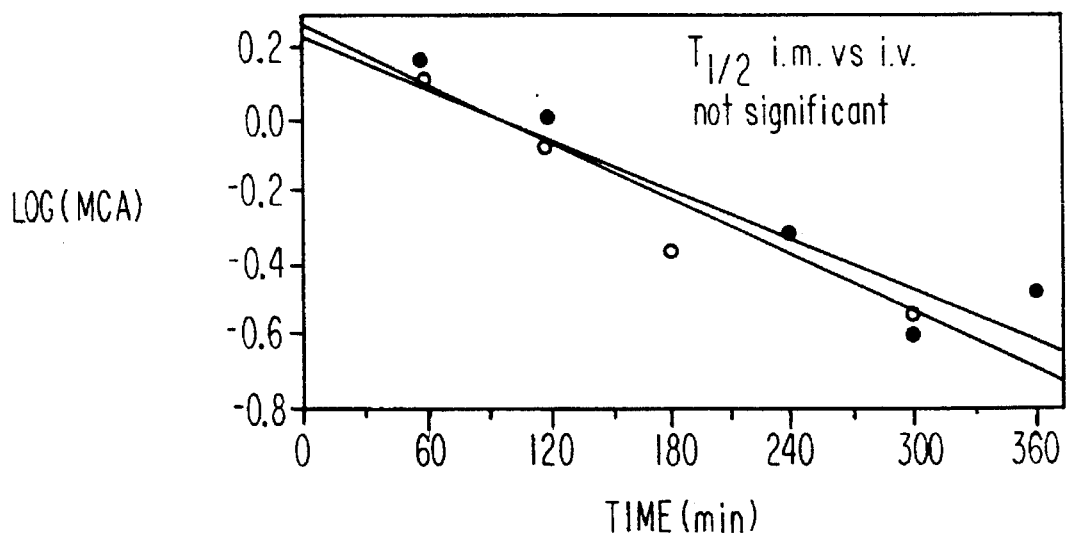
FIG. 1B is a graph of the same data with the serum concentrations of metoclopramide plotted as logarithmic values.

This example demonstrates the feasibility of substituting high dose i.m. injection of metoclopramide for the i.v. route of administration in the treatment of emesis or as an enhancer of radiation and chemotherapy. The bioavailability of high dose i.m. injection of metoclopramide is nearly 100% which establishes this route of administration as dose equivalent to i.v. administration (FIGS. 1A and 1B). One skilled in the art would not have anticipated this result, but would have instead expected a time delay due to absorption of the drug through the muscle tissue into the blood. Dose timing is an important consideration when establishing the effectiveness of metoclopramide as an enhancer of radio- and chemotherapy (Lybak et al., Anti-Cancer drugs 2: 375–382, 1991; Lybak et al., Acta Oncologica 31: 469–474, 1992). Therefore, these data teach that clinical results determined by i.v. administration of metoclopramide can be extrapolated to include i.m. administration, because the serum levels of drugs are generally regarded as to directly relate to their pharmacological effects.

EXAMPLE 2

This example discloses that there is a considerable difference between acidic and neutral forms of metoclopramide hydrochloride solutions in regard to the reaction of muscle tissue to i.m. injection. For example, acidic metoclopramide hydrochloride solutions caused discoloration, stiffness and pain in the injection area at doses of 7–28 mg/kg whereas neutral metoclopramide hydrochloride solutions induced no visible symptoms at all within this dose range (Table 1).

TABLE 1

Symptoms of the local tissue reaction to high dose intramuscular (i.m.) injection of acidic and neutralized forms of metoclopramide (MCA) hydrochloride solutions in Fisher 344 rats.

| MCA Dose | MCA pH Form | Rats Tested (n) | Number of Injections | Symptom Score[a] Value | n |
|---|---|---|---|---|---|
| 28 mg/kg i.m. | Acidic | 8 | 6 | ++++ | 8 |
| Saline i.m. | — | 8 | 6 | 0 | 0 |
| 28 mg/kg i.m. | Neutral | — | — | n.d. | n.d. |
| Saline i.m. | — | — | — | n.d. | n.d. |
| 14 mg/kg i.m. | Acidic | 9 | 6 | +++ | 9 |
| Saline i.m. | — | 9 | 6 | 0 | 0 |
| 14 mg/kg i.m. | Neutral | 5 | 10 | 0 | 0 |
| Saline i.m. | — | 5 | 10 | 0 | 0 |
| 7 mg/kg i.m. | Acidic | 10 | 10 | + | 6 |
| Saline i.m. | — | 10 | 10 | 0 | 0 |
| 7 mg/kg i.m. | Neutral | 5 | 10 | 0 | 0 |
| Saline i.m. | — | 5 | 10 | 0 | 0 |
| 3.5 mg/kg i.m. | Acidic | 10 | 10 | 0 | 0 |
| Saline i.m. | — | 10 | 10 | 0 | 0 |
| 3.5 mg/kg i.m. | Neutral | 10 | 10 | 0 | 0 |
| Saline i.m. | — | 10 | 10 | 0 | 0 |

[a]The symptom scoring system is presented in the section identified as the Detailed description of the invention.
n = number of animals with symptoms.

EXAMPLE 3

This example adds additional support to the data presented in Example 2. In this case edema, acute inflammation, bleeding and necrosis were the endpoints for comparing the acute histopathological effects of acidic and neutral forms of metoclopramide hydrochloride solutions. It is quite evident from the data presented in Table 2 that the neutral form is less toxic and consequently more safe than the acidic form.

TABLE 2

Acute histopathology of the local tissue reaction to high dose intramuscular (i.m.) injection of acidic and neutralized forms of metoclopramide (MCA) hydrochloride solutions in Fisher 344 rats.

| MCA Dose | MCA pH Form | Rats Tested (n) | Number of Injections | Acute Histopathology Score[a] | | | |
|---|---|---|---|---|---|---|---|
| | | | | Edema | Acute Inflammation | Bleeding | Necrosis |
| 28 mg/kg i.m. | Acidic | 8 | 6 | 2.5 (2–3) | 1.5 (1–2) | 2.4 (1–3) | 0.8 (0–3) |
| Saline i.m. | — | 8 | 6 | 0 | 0 | 0 | 0 |
| 28 mg/kg i.m. | Neutral | — | — | n.d. | n.d. | n.d. | n.d. |
| Saline i.m. | — | — | — | n.d. | n.d. | n.d. | n.d. |
| 14 mg/kg i.m. | Acidic | 9 | 6 | 2.1 (1–3) | 1.8 (1–3) | 2.6 (1–3) | 0.6 (0–2) |
| Saline i.m. | — | 9 | 6 | 0 | 0 | 0.1 (0–1) | 0 |
| 14 mg/kg i.m. | Neutral | 5 | 10 | 0 | 0 | 0 | 0 |
| Saline i.m. | — | 5 | 10 | 0 | 0 | 0 | 0 |
| 7 mg/kg i.m. | Acidic | 10 | 10 | 0.1 (0–0.5) | 0 | 0 | 0 |
| Saline | — | 10 | 10 | 0.1 (0–1) | 0.1 (0–1) | 0.1 (0–1) | 0 |
| 7 mg/kg i.m. | Neutral | 5 | 10 | 0 | 0 | 0 | 0 |
| Saline i.m. | — | 5 | 10 | 0 | 0 | 0 | 0 |
| 3.5 mg/kg i.m. | Acidic | 10 | 10 | 0 | 0 | 0.1 (0–1) | 0.1 (0–1) |
| Saline i.m. | — | 10 | 10 | 0 | 0 | 0 | 0 |
| 3.5 mg/kg i.m. | Neutral | 10 | 10 | 0 | 0 | 0 | 0 |
| Saline i.m. | — | 10 | 10 | 0 | 0 | 0 | 0 |

[a]The acute histopathology scoring system is presented in the section identified as the Detailed description of the invention
The numbers in parentheses are the range values.
n.d. = not determined

EXAMPLE 4

This example is likewise comparable to the data presented in Examples 2 and 3. Here the chronic pathology resulting from repeated i.m. injections in the same area of thigh was evaluated. Again chronic inflammation and muscle degeneration was less in those animals receiving neutral metoclopramide hydrochloride solution than was observed with the acidic form (Table 3).

TABLE 3

Chronic histopathology of the local tissue reaction to high dose intramuscular (i.m.) injection of acidic and neutralized forms of metoclopramide (MCA) hydrochloride solutions in Fisher 344 rats.

| MCA Dose | MCA pH Form | Rats Tested (n) | Number of Injections | Chronic Histopathology Score[a] Chronic Inflammation | Muscle Degeneration |
|---|---|---|---|---|---|
| 28 mg/kg i.m. | Acidic | 8 | 6 | 2.2 (2–3) | 2.0 (2) |
| Saline i.m. | — | 8 | 6 | 0.2 (0–1) | 0 |
| 28 mg/kg i.m. | Neutral | — | — | n.d. | n.d. |
| Saline i.m. | — | — | — | n.d. | n.d. |
| 14 mg/kg i.m. | Acidic | 9 | 6 | 2.8 (2–3) | 1.6 (1–3) |
| Saline i.m. | — | 9 | 6 | 0.1 (0–1) | 0 |
| 14 mg/kg i.m. | Neutral | 5 | 10 | 0.5 (0–1) | 0.7 (0.5–1) |
| Saline i.m. | — | 5 | 10 | 0 | 0 |
| 7 mg/kg i.m. | Acidic | 10 | 10 | 0.9 (0–2) | 1.4 (0–2) |
| Saline | | 10 | 10 | 0.3 (0–2) | 0.5 (0–2) |
| 7 mg/kg i.m. | Neutral | 5 | 10 | 0.6 (0.5–1) | 0.6 (0.5–1) |
| Saline i.m. | — | 5 | 10 | 0 | 0 |
| 3.5 mg/kg i.m. | Acidic | 10 | 10 | 1.3 (0.5–2) | 1.3 (1–2) |
| Saline i.m. | — | 10 | 10 | 0.3 (0.5–1) | 0.2 (0–0.5) |
| 3.5 mg/kg i.m. | Neutral | 10 | 10 | 0.9 (0–1.5) | 0.8 (0.5–1.5) |
| Saline i.m. | — | 10 | 10 | 0.1 (0–0.5) | 0.1 (0–0.5) |

[a]The chronic histopathology scoring system is presented in the section identified as the Detailed description of the invention.
The numbers in parentheses are the range values.
n.d. = not determined

EXAMPLE 5

Figure 2:
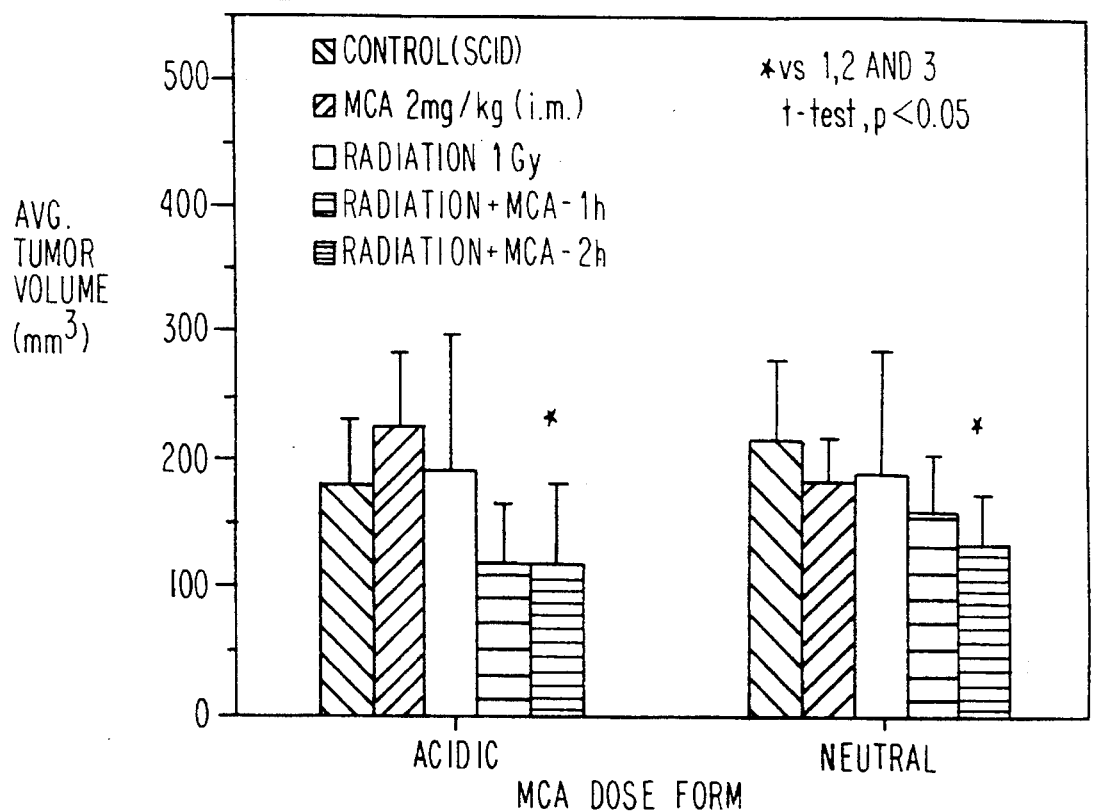
FIG. 2 is a bar graph illustrating the growth of human H-2981 lung adenocarcinoma tissue xenografted onto scid mice treated with 1 Gy radiation with and without metoclopramide administered by intramuscular injection as evaluated on day 18 after injection.

This example (FIG. 2) shows that the pharmacological property of radiosensitization is not altered by changing the pH of a high concentration solution (Lundbeck AB, Copenhagen) of metoclopramide hydrochloride from pH 3 to 4 (i.e. acidic form) and to pH 7.0 (i. e. neutral form). These data establish that undesirable side effects of metoclopramide can be reduced as evidenced by Examples 2–4 without a corresponding reduction in the pharmacological properties of metoclopramide.

EXAMPLE 6

Figure 3:
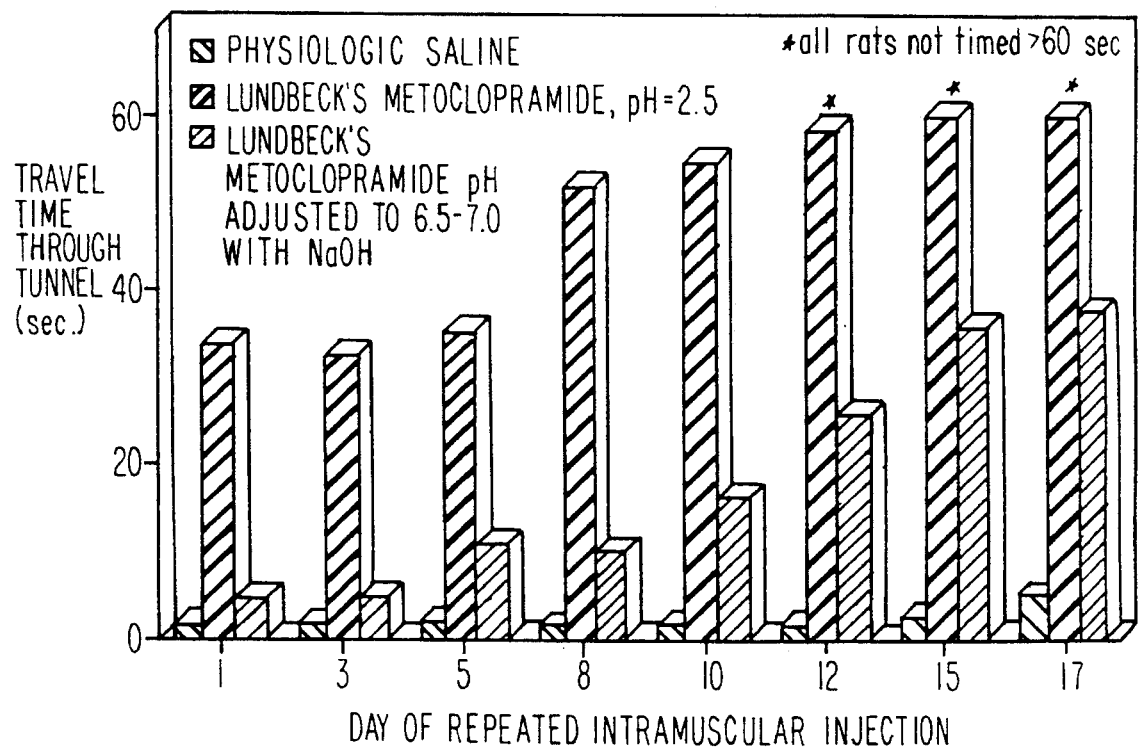
FIG. 3 is a bar graph illustrating the sedative effect of pH adjusted metoclopramide hydrochloride provided by Lundbeck AB (copenhagen) as a 100 mg/ml sterile injectable concentrate, in a test wherein five rats in each of the three treatment groups represented were given repeated intramuscular injections of saline or metoclopramide (14 mg/kg) three times per week excluding weekends and sedation was estimated 15 minutes after drug administration.

This example presents data demonstrating that when Lundbeck's commercial formulation of metoclopramide hydrochloride is administered i.m. before and after pH adjustment in the rat, there is a considerable reduction in the degree to which the rats become sedated if the formulation is at pH 6.5 to 7.0 (FIG. 3). Hence, these data teach that there is some chemical interaction of metoclopramide under acidic conditions that does not occur under near neutral conditions, where the result of this chemical interaction can be transported from the site of intramuscular injection through the blood to the receptors in the brain that can mediate a sedative effect.

EXAMPLE 7

This example discloses more precisely what is required to be present in the metoclopramide hydrochloride injectable solutions in order to induce the sedative effect in the rat. The data establish that if sterile injectable formulations of metoclopramide hydrochloride are below at least pH 4.5 and contain sodium ions in the form of either sodium chloride or sodium metabisulfite, there is an amplified extra-pyramidal sedative side effect that does not occur if the pH is maintained between 5.5 and 7.0 (Table 4).

TABLE 4

The sedation side effects in the rat caused by pH changes of various formulations of metoclopramide for sterile injection.

| Formulation of sterilized injectable solutions of metoclopramide[a] | | | | | |
|---|---|---|---|---|---|
| Metoclopramide monohydrochloride | Sodium meta-bisulfite | NaCl | $H_2O$ | pH | Sedation Index (Sec)[b] |
| (1) 100 mg | 0 | 0 | 1 ml | 4.2 | 3.0 ± 1.4 |
| (2) 100 mg | 0 | 0 | 1 ml | 6.5 | 4.4 ± 0.9 |
| (3) 100 mg | 2 mg | 0 | 1 ml | 3.2 | 29.2 ± 20.6* |
| (4) 100 mg | 2 mg | 0 | 1 ml | 6.5 | 4.0 ± 0.7 |
| (5) 100 mg | 0 | 9 mg | 1 ml | 3.5 | 31.3 ± 21.0* |
| (6) 100 mg | 0 | 9 mg | 1 ml | 4.5 | 34.4 ± 24.8* |
| (7) 100 mg | 0 | 9 mg | 1 ml | 5.5 | 4.6 ± 2.0 |
| (8) 100 mg | 0 | 9 mg | 1 ml | 6.5 | 5.4 ± 4.5 |
| (9) 100 mg | 2 mg | 9 mg | 1 ml | 3.6 | 40.4 ± 20.2* |
| (10) 100 mg | 2 mg | 9 mg | 1 ml | 6.5 | 4.6 ± 1.5 |

[a]all solutions were autoclaved at 115° C. for 30 minutes before use
[b]average travel time (mean ± SD) for 5 rats to complete a 8 × 10 × 45 cm tunnel. Group 5 had n = 10.
*t-test comparison to other groups, p < 0.05

It is to be understood that the invention is not limited to the procedures and embodiments hereinabove specifically set forth, but may be carried out in other ways without departure from its spirit.

What is claimed is:

1. A method of administering to a human patient material selected from the group consisting of phenothiazines, their acid addition salts, and mixtures thereof, comprising the steps of (a) providing a sterile injectable formulation comprising a liquid vehicle containing the material in solution, at a pH within a range of about 5.5 to 7.0, and (b) injecting the formulation intramuscularly into the patient in an amount for delivering to the patient a dose of about one to about 5 mg/kg of the material while the pH of the formulation is within said range.

2. A method according to claim 1, wherein the concentration of the material in the formulation is at least about 50 mg/ml.

3. A method according to claim 1, wherein said formulation contains $Na^+$ ions.

4. A method according to claim 1, wherein said formulation is essentially free of $Na^+$ ions.

5. A method of administering to a human patient material selected from the group consisting of, phenothiazines, their acid addition salts, and mixtures thereof, comprising the steps of (a) providing a sterile formulation, comprising a liquid vehicle containing the material in solution and also containing $Na^+$ ions, (b) adjusting the pH of said formulation for reducing the development of undesirable side effects caused by injecting the material, and (c) administering the formulation having the adjusted pH to the patient.

6. A method of administering to a human patient material selected from the group consisting of phenothiazines, their acid addition salts, and mixtures thereof, comprising the steps of (a) providing a sterile formulation, comprising a liquid vehicle containing the material in solution at a pH within a range of about 5.5 to 7.0, and (b) administering the formulation to the patient while the pH of the formulation is within said range.

7. A method according to claim 6, wherein the formulation is initially at a pH below 5.5, and wherein the providing step includes adjusting the pH of the formulation such that the pH is within said range.

8. A method of administering to a human patient material selected from the group consisting of, phenothiazines, their acid addition salts, and mixtures thereof, comprising the steps of (a) providing a formulation comprising a liquid vehicle containing the material in solution and essentially free of $Na^+$ ions, and (b) administering the formulation, essentially free of $Na^+$ ions, to the patient.

* * * * *